United States Patent [19]

Marple et al.

[11] Patent Number: 5,040,424

[45] Date of Patent: Aug. 20, 1991

[54] HIGH VOLUME PM$_{10}$ SAMPLING INLET

[75] Inventors: Virgil A. Marple, Maple Plain; Benjamin Y. H. Liu, North Oaks, both of Minn.

[73] Assignee: Regents of the University of Minnesota, Minneapolis, Minn.

[21] Appl. No.: 608,033

[22] Filed: Oct. 30, 1990

Related U.S. Application Data

[63] Continuation of Ser. No. 494,791, Mar. 12, 1990, abandoned, which is a continuation of Ser. No. 222,152, Jul. 21, 1988, abandoned.

[51] Int. Cl.$^5$ .............................................. G01N 1/00
[52] U.S. Cl. .................................................. 73/863.23
[58] Field of Search .......... 73/863.21, 863.22, 863.23, 73/863.25, 28; 55/270, 315, 318, 320; 209/133, 138

[56] References Cited

U.S. PATENT DOCUMENTS

| | | | |
|---|---|---|---|
| 3,518,815 | 7/1970 | McFarland et al. | 73/863.22 |
| 3,949,594 | 4/1976 | Treaftis et al. | 55/270 |
| 4,133,202 | 1/1979 | Marple | 73/28 |
| 4,301,002 | 11/1981 | Loo | 209/143 |
| 4,321,822 | 3/1982 | Marple et al. | 73/28 |
| 4,382,808 | 5/1983 | Van Wormer, Jr. et al. | 73/863.23 |
| 4,461,183 | 7/1984 | Wedding | 73/863.21 |
| 4,544,386 | 10/1985 | Trayford, III et al. | 73/863.25 |
| 4,653,773 | 4/1972 | Childs | 73/28 |
| 4,670,135 | 6/1987 | Marple et al. | 509/143 |
| 4,737,171 | 4/1988 | Courbon | 55/270 |
| 4,767,524 | 8/1988 | Yeh et al. | 73/28 |

OTHER PUBLICATIONS

McFarland et al., "Particle Collection Characteristics of a Single-Stage Dichotomous Sampler", Environmental Science & Tech., vol. 12, No. 6, Jun. 1978.
Aerosols: Research, Risk Assessment and Control Strategies, Second U.S. Dutch International Symposium, Williamsburg, Va., The United States, May 19-25, 1985.
Federal Register, vol. 49, No. 55, Tuesday, Mar. 20, 1984, Proposed Rules.
NASA Tech. Brief, No. 4, Aug. 1974, p. B74-10080; R. B. King: "Improved high volume air sampler".

Primary Examiner—Robert Raevis
Attorney, Agent, or Firm—Kinney & Lange

[57] ABSTRACT

A sampling inlet for sampling aerosols in atmospheric air comprises an inlet housing that has an air flow and an inertial particle classification device in a series flow path from an inlet opening in the sampler to a filter which collects the material. The sampler is a classification device of the virtual impactor type, utilizing nozzles that receive the flow carrying the aerosols, and a receiver tube that is aligned with the nozzle and spaced therefrom, with a major portion of flow being diverted from the space between the nozzle and the receiver tube. The heavier particles are carried by inertia into the receiver tube and then are carried off by minor flow of fluid that passes through the receiver tubes.

20 Claims, 5 Drawing Sheets

HIGH VOLUME PM$_{10}$ SAMPLING INLET

This is a continuation of application Ser. No. 07/494,791 filed on Mar. 12, 1990, now abandoned, which in turn was a continuation of application Ser. No. 07/222,152, filed on July 21, 1988, now abandoned.

BACKGROUND OF THE INVENTION

1. Field of the Invention

The present invention relates to an inlet housing for a particle sampling apparatus in high volume atmospheric flows.

2. Description of the Prior Art

A common method of sampling atmospheric aerosols is to use a high volume sampler in an inlet to a flow system which has a flow rate of 40 cubic feet per minute. This flow rate has been established as a standard, and the particles larger than a standard cutoff size are collected and are then weighed to determine the mass concentration of the particles, or the particles collected may be otherwise analyzed.

In recent years the Environmental Protection Agency (EPA) has established that a particle separating inlet which removes all of the particles that are larger than 10 microns from the flow before collecting the particles for analyzers should be developed. The sampling characteristics for such inlet must be substantially insensitive to wind direction and wind speed. The Federal Register, Volume 49, No. 55 for Tuesday Mar. 20, 1984 contains the proposed rules for testing such sampler inlet.

There have been two presently known commercial sampling devices that comprise high volume inlets intended to separate all particles larger than 10 microns from the flow. One is a 10 micron size selective Hi-Vol sampler made by Sierra-Andersen, Inc. of Atlanta, Ga. and the second is a PM$_{10}$ inlet that is sold by Wedding & Associates, Inc. of Fort Collins, Colo. The Sierra-Andersen device utilizes an absorber, "no bounce" surface that has a light oil on it to collect particles that impact upon the surface. The larger particles may, however, bounce off the surface and then they are carried through the sampler. The absorber surface (or impaction plate) used in the devices requires periodic reoiling in order to operate satisfactorily. The Wedding inlet is a cyclonic device with the 10 micron diameter particles, and larger, being precipitated on a surface of a cylinder against which the air is spiralling downward as it flows through the inlet. The surface of the cylinder is called a "perfect absorber no-bounce surface" which also comprises a porous material saturated with a light oil, with its practical limitations in operation.

In both of the inlet devices described, the particles that pass through the inlet proceed to a standard eight by ten inch high volume filter.

The performance of these inlets depends on the condition of the oiled surface, that is, whether or not it is clean or covered with particles, and the collection surfaces require servicing in the form of replacing the porous surface material, cleaning it, or adding more oil.

Particle separation utilizing impactors has been well known in the art. For example, U.S. Pat. Nos. 4,133,202 and 4,321,822 show impactor devices that depend on inertia for separation of particles. Also, U.S. Pat. No. 4,301,002 shows a virtual impactor which includes means for inertial separation or classification of particles in an air flow.

U.S. Pat. No. 4,670,135, issued to the present inventors, also shows inertial separation in virtual impactors.

A paper presented by Benjamin Y. H. Liu et al. was published as Chapter 10 of the proceedings of "The Second United States—Dutch International Symposium on Aerosols", held in Williamsburg, Va. on May 19-24, 1985 and entitled "Aerosol Sampling and Sampling Inlets", discloses such inlets and shows the welding inlet and a form proposed by the authors.

Thus, a service-free inlet that provides an accurate "cut" of particles at 10 microns is desired.

SUMMARY OF THE INVENTION

The present invention relates to a high-volume aerosol sampling inlet housing which provides smooth inlet flow to a 10 micron classification device in a high volume flow in a simple, trouble-free manner. The high volume sampler with which the inlet is used establishes a high flow, for example, 40 cubic feet per minute. The air flow into the inlet has a standard 40 cubic feet per minute leading to the high volume sampler which requires a secondary inlet flow of about two cubic feet per minute needed for particle classification. The two cubic feet per minute flow is exhausted at a separate outlet and is not connected to the standard high volume sampler. Thus, a total flow of 42 cubic feet per minute enters the inlet.

The entrance opening to the inlet is an annular opening below a dome cover. Screens are provided to keep any bugs or large debris from entering the inlet housing. The debris-free air flow is passed through the desired impactor device and the large particles will be collected with the secondary outlet flow of only two cubic feet per minute while the smaller particles are carried out by the major flow of 40 cfm to the high volume sampler filter placed below. The larger particles are thus inertially separated from the major flow and are flushed by the smaller secondary or minor flow. The major flow through to the high volume sampler is maintained at the standard 40 cubic feet per minute.

The particles in the inlet air stream are separated into size classifications larger and smaller than 10 microns.

The large particles that are flushed out with the two cubic feet per minute flow can either be removed from the air stream by a second filter, or analyzed in a conventional impactor or some other device, or may be allowed to pass through the air pump and be blown back into the atmosphere. In the invention disclosed, there is no need to collect the large particles on a surface, so no oiled surfaces are required and thus the maintenance is very low.

Preferred forms of the invention use high volume virtual impactors for particle separation. Impactors can be placed in series, if desired. Also, as shown, the separation of particles can be done with an impactor positioned above the inlet opening to the sampler. The inlet housing is well protected from rain water through the use of a relatively large dome, and any water particles that might enter in the flow are of large size so that they are separated out along with the larger solid particles and do not provide a hazard to the data collected on the high volume filter.

The inlet of the present invention is simple, with an annular opening for incoming air and a virtual impactor (classification) section required, to give a substantially exact particle cutoff size, depending upon selection of the minor flow volume and the spacing between the nozzle and receiving tube.

DETAILED DESCRIPTION OF THE PREFERRED EMBODIMENTS

Figure 1:
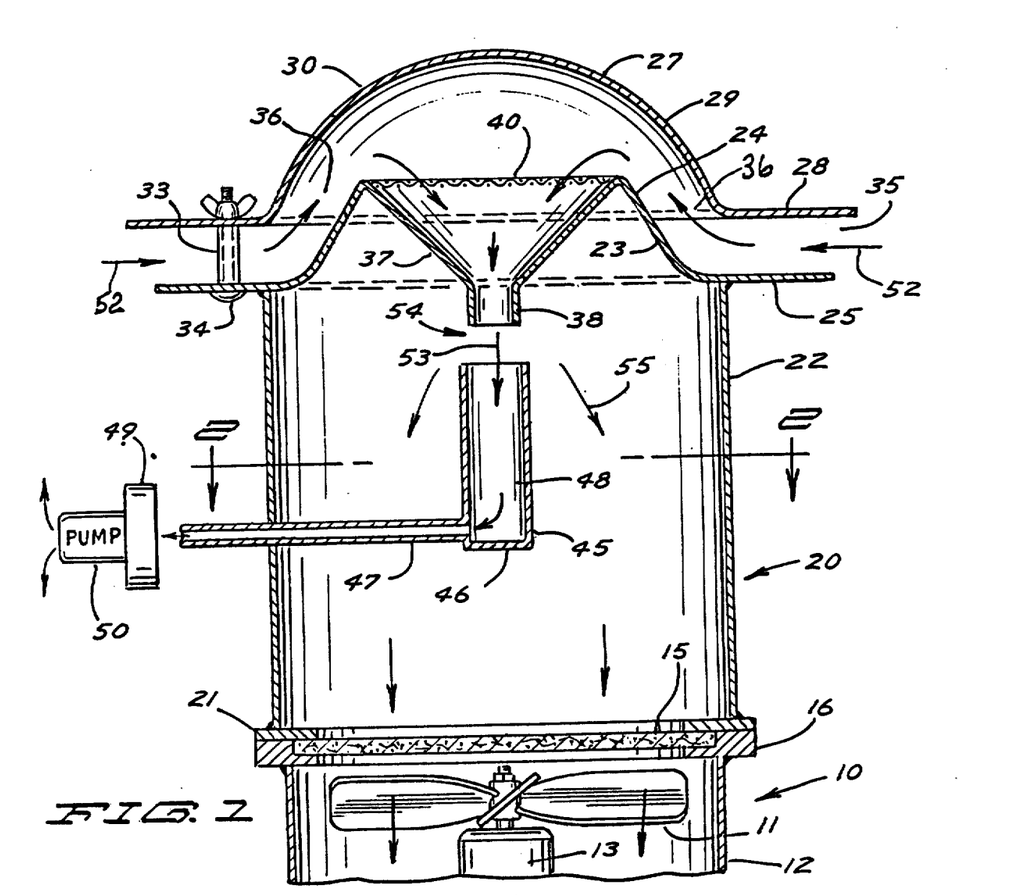
FIG. 1 is a vertical cross-sectional view of a simplified inlet construction for a high volume sampler made according to the present invention.
Figure 2:
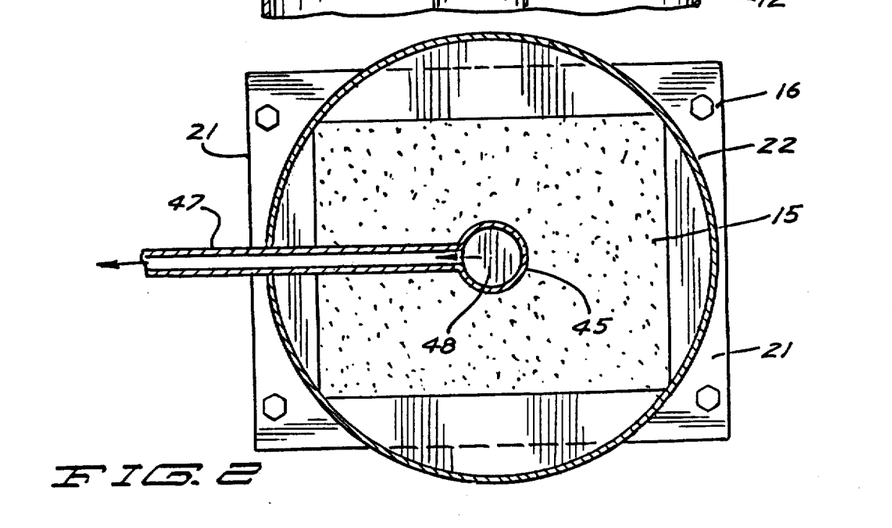
FIG. 2 is a sectional view taken as on line 2—2 in FIG. 1.

A high volume sampler indicated generally at 10 comprises an air pump 11 mounted in a duct 12, which pump as shown is a fan that has a controlled volume. In the form shown, the volume from the pump 11, which is driven by motor 13, is a standard flow of 40 cubic feet per minute that passes through the duct 12. The sampler includes a standard eight by ten inch filter indicated generally at 15 that is mounted on a suitable frame 16 above the pump 11, and through which the 40 cubic feet per minute air flow will pass so that particles that are carried by the air flow will be filtered before entering the duct 12. Nominally, the standard eight by ten inch high volume filter is used for collecting particles smaller than 10 microns. An inlet housing indicated generally at 20 has a base flange 21 that fits over the filter 15 and is held in place with suitable capscrews to frame 16 in a conventional manner.

The inlet housing 20 has a cylindrical wall 22, and the upper end of housing 20 is provided with a flow guide wall 23 that covers the top of the housing 20, and has its outer edges formed in a smoothly contoured upwardly and inwardly extending, annular flow directing wall 24. On the exterior of the housing and surrounding the housing, there is a flat peripheral flange or rim 25 which forms part of the wall 23 and which extends outwardly from the housing 20 a selected distance.

A dome-shaped cover 27 overlies the wall 23, and has an outer peripheral flange or rim 28 that is spaced upwardly from and is generally parallel to the flange 25, but is of larger outer diameter. The cover 27 has an inlet flow directing wall section 29 that is complementary in slope to the wall section 24 and is spaced therefrom to form an air flow passageway. The cover 27 also has a central dome portion 30 that overlies the central portion of the wall 23. The cover 27 can be supported relatively to the wall 23 with suitable stand-off or spacer members 33 and held in place with suitable capscrews 34 so that the cover 27 can be removed if desired. The cover 27 is held in place to define an annular inlet air flow opening 35 which extends all the way around the housing, and as stated, also to define an inlet air flow passageway 36 with respect to the wall portion 24 that is directed upwardly from the annular inlet opening 35.

The center portions of the wall 23 are formed to extend downwardly in a conical wall portion 37, which terminates in a cylindrical nozzle 38 which is centered on the central axis of the housing 20. The conical wall portion 37 provides a Venturi effect and accelerates the incoming air flow passing through nozzle 38.

A screen 40 is provided over the upper end of the conical wall 37 to separate out large debris, bugs, and the like from the air flow that enters the inlet opening 35 and passes through the passageway 36.

Particle classification is achieved using a cylindrical tube 45, which is coaxial with the nozzle 38, and which is positioned, aligned with and spaced below the nozzle 38. The receiving tube 45 is of slightly larger diameter than the nozzle 38, and has a desired axial length. It has a closed bottom wall 46. A laterally extending minor flow tube 47 is open to the interior chamber 48 of the receiver tube 45. The flow tube 47 extends out through the side wall of the housing 20. Tube 47 can be made rigid so that it will support the receiving tube 45, or the receiving tube can be supported on individual spider type radial support members extending out to wall 22, if desired.

The minor flow tube 47 is connected to a low volume pump 50 that draws a small amount of flow through the tube 47, and this flow passes through a filter 49 if desired, that can collect particles carried by the minor flow passing through the tube 47.

When the high volume particle sampler is being used, the pump 50 is operating to draw approximately five percent of the standard high volume total incoming flow through the tube 47. The major flow passes through the filter 15 as controlled by the pump 11. For example, a total flow of 42 cubic feet per minute is provided by the two pumps 11 and 50. The total flow enters through the annular inlet flow opening 35 as indicated by the arrows 52, and the flow then will flow smoothly upwardly between the wall sections 24 and 29 and through passageway 36. The flow will pass through the screen 40, and into the conically-shaped Venturi member 37, where the air is accelerated before it passes out through the nozzle 38, which is directly in line with the receiving tube 45.

The flow direction out nozzle 38 is as indicated by the arrow 53, and because the major flow must pass out through the spacing 54 between the lower end of the nozzle 38 and the upper end of the receiving tube 45, particles which have high inertial forces will be carried down into the receiver tube a greater amount or greater distance than lighter particles. The larger particles have larger inertia and therefore longer stopping distances, and penetrate farther into the receiving tube than the smaller particles. By proper selection of the sizes of nozzle 38 and the receiving tube 45, as well as the spacing 54, the particles that are larger than 10 microns can be selectively retained in the receiver tube 45, while the smaller particles pass outwardly as indicated by the arrows 55. The smaller particles carried out in the flow indicated by arrow 55 are then collected by the filter 15 for examination.

The minor flow of two cubic feet per minute through the minor flow tube 47 flushes the larger particles out of the receiving tube 45, where they can be passed through the filter 49 for collection, or analyzed in a conventional particle impactor or some other device. The larger particles could be allowed to pass through the pump and be discharged into the atmosphere.

There are no moving parts for the classification nozzle 38 and receiving tube 45, but they provide a very precisely defined cutoff of particle sizes between those that are collected on the filter 15 and those which are removed from the major flow through the receiving tube 45.

The air flow inlet opening 35 is also quite well protected from rain water passing through the classification system. The domed cover 27, as can be seen, sheds rain water and the rim 28 is of larger diameter than the rim 25, so that water will drip off the dome and not tend to enter the air flow inlet opening 35. If water is carried into the inlet opening 35, it must go upwardly across the upwardly extending, annular surface portions 24, where it will tend to collect and will then drain out of the inlet opening. It is generally expected that no water will reach the screen 40. If it does, the drops are almost certain to have a size larger than 10 microns and will be removed by the classification system comprising receiving tube 45, as will any other large particle. Such water will be exhausted or purged out through the minor flow tube 47 so that it does not provide a hazard to the data collected on the high volume filter 15.

FIG. 3 illustrates a second and preferred form of a high volume sampler made according to the present invention, which utilizes a virtual impactor for separating out larger than 10 micron particles, and also shown optionally, a series separation with a 2.5 micron cutoff virtual impactor that can be mounted in place in the outer housing of the sampling inlet.

The high volume particle sampler indicated generally at 60 is shown on a standard height stand 61 that can be used for mounting samplers in exterior locations. The stand has air outlet openings in the lower portions thereof. A throat section 62 is mounted on the top of the stand, and in normal applications a standard high flow filter indicated at 63 will be mounted on an annular divider wall or rim 64 at the bottom part of the throat. A suitable blower or pump 65 is mounted below divider wall or rim 64, to draw the desired amount of air through the filter 63, generally in the range of 40 cubic feet per minute. The filter 63 and blower or pump 65 can be oriented as shown in FIG. 1.

The throat 62 supports an inlet assembly indicated generally at 71 which is similiar to the inlet of the first form of the invention, but which uses a high volume vertical impactor shown generally at 80 for making a 10 micron cutoff of particles. The vertical impactor is formed as part of the inlet assembly and includes an annular flange 66 that has a horizontal portion 66A which extends outwardly from the periphery of the throat 62. The flange 66 has a curved annular intermediate section 68 that curves from a horizontal outer section 66A, inwardly and up to a vertical section 69. The vertical section 69 of the flange 66 then terminates as a cylindrical wall that has a cover plate thereon indicated generally at 70 that supports the nozzles for the impactor assembly which will be more fully explained.

The inlet flange 66 and the impactor 80 are covered with a dome-shaped housing or cover 73 that has an annular flange 74 that overlies the horizontal section 66A, and defines an inlet opening 75 that is annular around the top portion of the throat 62. The cover 73 is supported relative to the plate 66 with suitable stand-off members 76, for example three or more stand offs positioned around the assembly can be used in the same manner as that previously explained and can be released quickly for removing the housing or cover 73.

The cover 73 has a large opening (coarse) annular screen 78 formed therein that aligns with the vertical section 69 of the inlet wall 66. The atmospheric air (fluid) to be sampled coming in through the inlet opening 75, and has to pass through screen 78, which will filter out leaves and large debris.

The curved section 68 of flange 66 is curved smoothly, so the aerosol particles carried by the inlet air flow (illustrated by arrow 79) will not impinge the surface of flange 66 and be forced to drop out. Thus, there is no impaction phenomena at the inlet itself. The upper edge of the cylindrical wall section 69, as shown, preferably extends above the plane of the flange 74, to prevent particles from entering horizontally, such as wind driven raindrops or the like, where it would pass directly into the impactor apparatus 80. As shown, the spacing of the upper edge of the wall section 69 above flange 66A is approximately equal to the radial width of the annular flow channel or throat through which the air flows to get into the impactor apparatus.

The air flow coming in the inlet 75 then moves up and around a chamber formed at 81, above the impactor cover plate 70. The plate 70 forms an inlet nozzle support plate for the virtual impactor 80. As shown, the impactor nozzle arrangement is substantially similar in construction to that shown in U.S. Pat. No. 4,670,135. The blower or pump 65 draws air through the throat 62 and impactor, to cause the air inflow through inlet 75. The flow path requires the air to flow through a plurality of inlet nozzles 86 (see FIGS. 4 and 5) arranged annularly around the central axis of plate 70. The flow equalizes so that each of the inlet nozzles 86 carries a portion of the flow. The only flow path from the inlet 75 through the blower 65 is through the virtual impactor inlet nozzles 86. The nozzles 86 accelerate the flow, and are each axially aligned with corresponding receiver tubes 87. Each of the receiver tubes 87 is supported in a wall 90 that is parallel to cover plate 70 and spaced from the cover plate. The outer edge of wall 90 joins the cylindrical wall portion of flange 66 (see FIG. 5). An annular wall 90A also joins wall 90 at the periphery of a central opening in wall 90. The annular wall 90A joins an annular ring base wall 92. An enclosed chamber 91 is formed to the outside of the wall 90A and is defined by wall 90, throat section 68, wall 92 and the wall 90A.

The interior of annular wall 90A defines an annular opening 93 below cover plate 70. The major air flow will pass from nozzles 86 laterally and through interior opening 93, into the throat 62, and as shown through the filter 63. Alternately, the filter 63 can be positioned at the lower end of opening 93 if desired. The small particles can be counted, or analyzed in other ways.

A minor flow is established with a blower or pump 88 from the chamber 91. This flow path has a particle collector or filter 97 in the flow path. Particles above 10 microns (or other cut size) will pass into receiver 87 and be carried out with the minor flow from chamber 91. The blower 88 will provide a flow which is a known fraction of the major flow. For example, a 40 CFM major flow and a minor flow of about 2 CFM is used.

Figure 3:
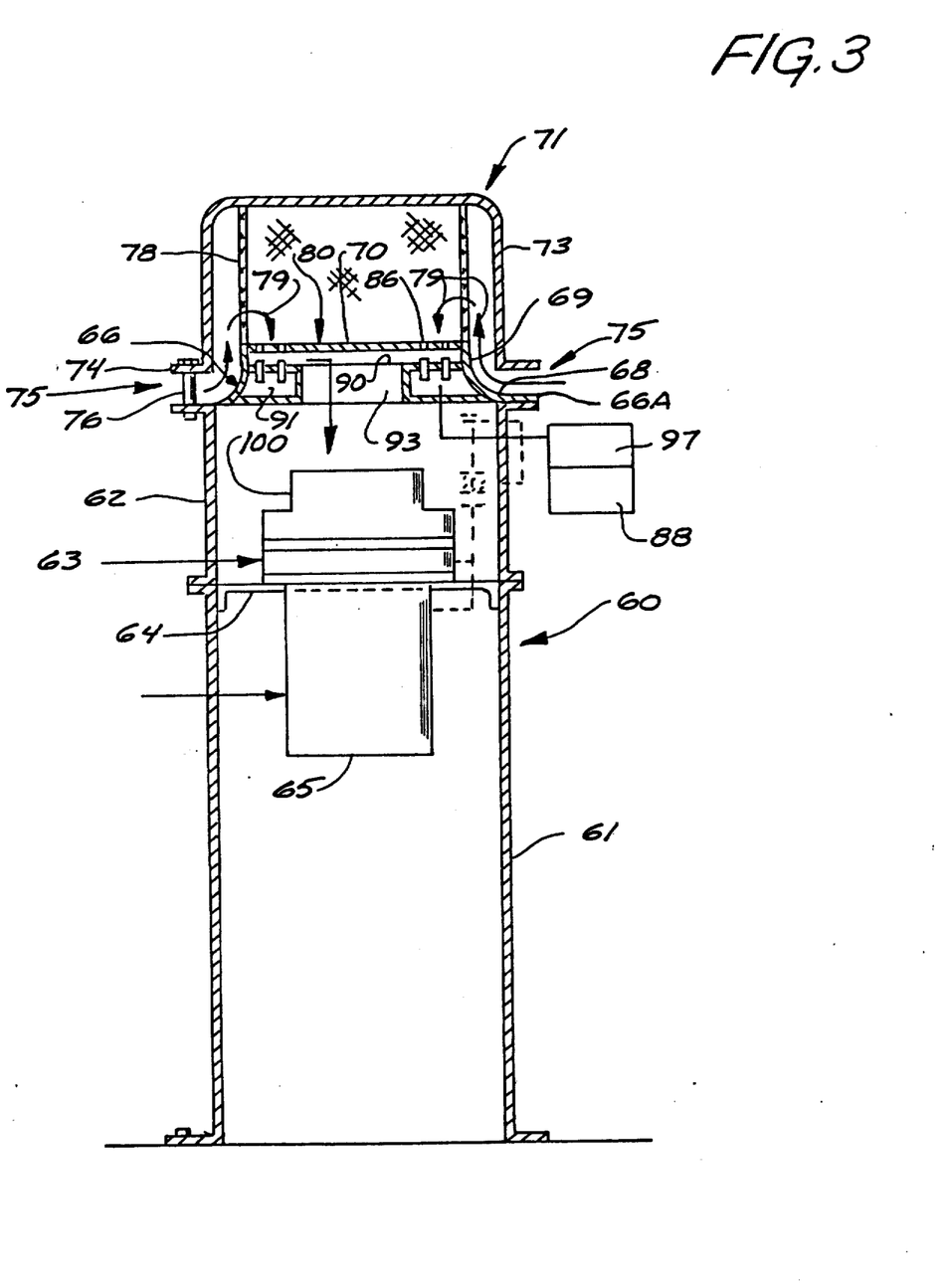
FIG. 3 is a vertical sectional view of a typical aerosol sampling inlet made according to the present invention utilizing a virtual impactor for 10 micron particle size cutoff, with an optional 2.5 micron size virtual impactor illustrated in place therein.
Figure 4:
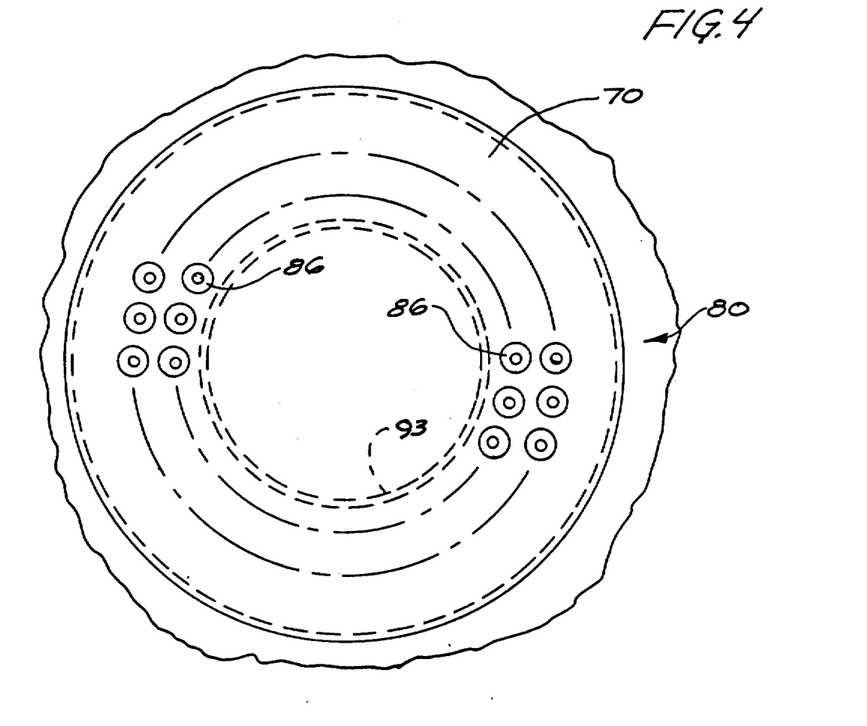
FIG. 4 is a sectional view taken as in line 4—4 in FIG. 3.
Figure 5:
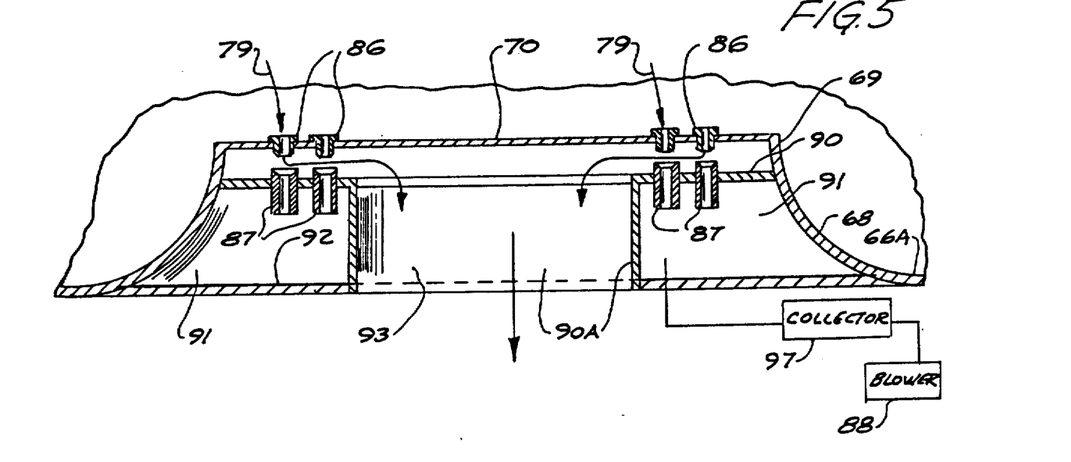
FIG. 5 is an enlarged sectional view taken generally along the same line as FIG. 1, with a typical virtual impactor used shown in cross section.

The virtual impactor assembly 80 is made so that it will provide a 10 micron particle cutoff size. The large particles in filter or collector 97 can also be analyzed, counted, and otherwise processed or discarded as desired.

An alternate auxiliary impactor indicated generally at 100 can be made the same as that shown in U.S. Pat. No. 4,670,135 to provide a different particle size cutoff, for example, 2.5 microns, if desired. The minor flow from the optional impactor can be provided by a separate blower, and the filter 63 then will collect the main flow after the last separation.

It is to be understood that the filter 63 will be used to collect the particles below 10 microns if the auxiliary impactor 100 is not used. The flow from first impactor 80 would then pass directly through the filter 63 and the particles collected. If the auxiliary impactor is used, particles below the 2.5 micron cutoff will be collected on filter 63.

The auxiliary flows for the virtual impactor 80 on the auxiliary impactor 100 flushes the particles out as described in connection with the first form of the invention.

Here, the housing or cover 73 also has a flange 74 that can be made to extend outwardly beyond the edge of wall 66A if desired, and the surface of the inlet throat sections 69 and 68 shed rain water. The rain water has to go across the curved surface portions 68 and up the vertical wall 69 to enter the impactor system, so that there is a tendency for rainwater to collect and then drain back down. The reason for having the upper edge of the cylindrical wall portion 69 above the flange 74 is to ensure that water being carried in by strong winds and moving horizontally will not merely be carried into the particle classification impactor and become collected along with the particles.

The virtual impactor again provides for inertial collection means in the standard size collection housings for a 10 micron particle devices.

Figure 6:
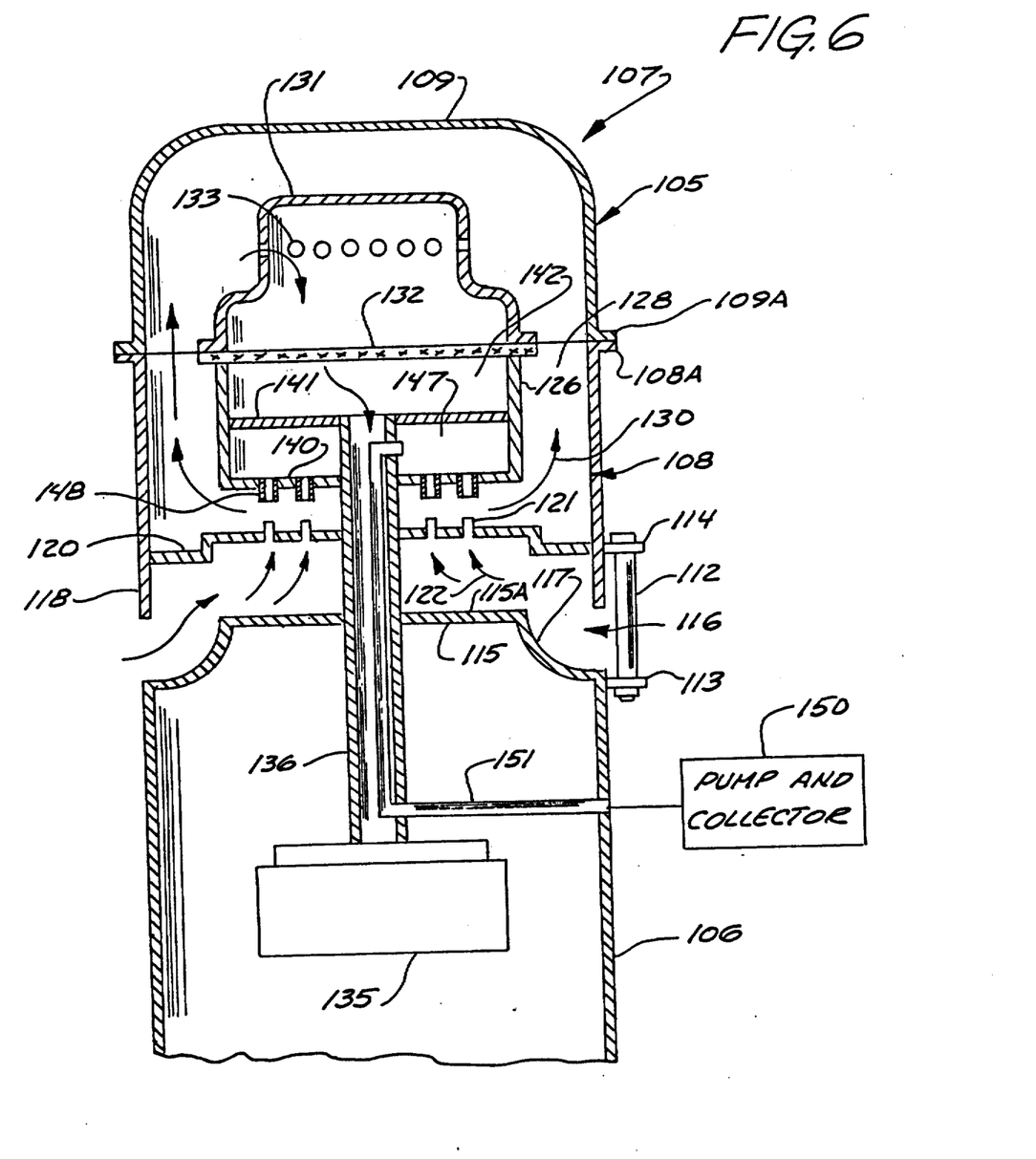
FIG. 6 is a vertical sectional view of a further modified form of the invention showing an impactor inverted from FIG. 3.

In FIG. 6, a further modified form of the invention is shown, and is illustrated somewhat schematically. The sampling inlet 105 is mounted onto a throat tube member 106 that is shown only schematically and which can be supported in the same manner as that shown in previous forms of the invention. The throat tube member 106 is a tubular housing that forms a support housing and which has an upper housing 107 mounted thereon. Upper housing 107 is made into two sections comprising a virtual impactor-particle separator section 108, and a removable cover housing section 109. The section 108 and section 109 are joined by suitable flanges 108A and 109A that can be bolted together or attached with quick coupling fasteners. The flanges 108A and 109A can be gasketed to prevent air flow at their junction plane.

The housing 107 is supported on suitable standoff members 112, that can extend from small ears 113 fixed on the throat tube member 106, and ears 114 that can be attached to the lower end of the housing section 108.

In this form of the invention, an upper end wall 115 of the throat tube member 106 defines a lower portion of an inlet opening 116, which is an annular opening as previously explained. The wall 115 has a curved peripheral inlet flange 117 that curves upwardly to direct incoming flow upwardly, and also to block rain water and the like from going directly into the interior portions of the inlet opening. The housing section 108 has a skirt 118 that extends downwardly to at least the same level as the plane of the upper center surface 115A of the wall 115. The center surface portion 115A is surrounded by the curved flange 117. This also protects against rain coming in through the inlet opening 116.

The virtual impactor, which provides particle separation, is within the annular enclosing wall of section 108. The lower end of the tubular section 108 is closed off with a cross wall 120. The cross wall 120 is spaced above wall 115 and has a plurality of nozzles 121 therein which are arranged around the central axis of the plate or wall 120, and have tapered inlets that will receive air flow which is indicated generally by the arrows 122. The nozzles have central axes that are vertical.

An inner impactor housing 126 has an annular wall therearound, which is closed from the inner surface of the wall of the housing section 108 to define an annular air flow passageway 128, so that air coming in through the nozzles 121 will be urged to flow laterally and upwardly as indicated by the arrows 130. A cap member 131 is mounted above the wall 126 in a suitable manner, and a high volume filter 132 is positioned between the upper end of the wall 126 and the cap 131. The cap 131 has a plurality of openings 133 therein, through which the air can flow, as it is drawn by a pump or blower 135.

In this form of the invention, the pump or blower 135 is connected to a conduit 136 that sealingly passes through the center of the wall 115, and the wall 120, and which also passes through walls 140 and 141 which define portions of a minor flow chamber. The wall 141 is sealingly fixed to the wall 126 and forms a plenum chamber 142 above wall 141. The chamber 142 is below filter 132 and is open to the bottom side of the filter 132. Air flow drawn by the pump 135 that comes in through the inlet 116 passes through the nozzles 121, and the major flow goes through the annular passageway 128, through the openings 133 in the cap 131 and then through the filter 132 so that particles are collected on the filter 132. This air is then passed through the plenum chamber 142 into the conduit 136 and carried out by the pump 135, which will discharge it in the normal manner.

The minor flow for classification is taken from the minor flow chamber 147 which is defined by the peripheral wall 126, and by the walls 140 and 141. The wall 140 has a number of receiver tubes 148 mounted therein and which are axially aligned with the respective nozzles 121. The minor flow is created by a pump and collector arrangement indicated generally at 150 that draws material through a conduit 151, which as shown passes into and is sealed from the interior of the conduit 136. The conduit 151 is connected to the minor flow chamber 147. The volume of the minor flow created by the pump and collector 150 can be adjusted so that the particles that are carried by the nozzles 121 upwardly into the receiving tubes 148 will be carried through the minor flow chamber 147 and purged out through the pump and collector 150.

An advantage of this type of arrangement is that by taking off the cover 109, the cap 131 is accessible easily and the filter 132 also is accessible so that the filter and the collected particles thereon can be easily removed and analyzed. This makes servicing the sampling inlet easier and less burdensome.

The wall 120 is attached to the housing wall for the housing section 108 in any desired manner, and the minor flow chamber, and the overlying filter 132 can be supported as desired.

The conduit 136 can be sized to permit adequate air flow for the separation of the particles at 10 microns.

It should be noted that when utilizing the impaction nozzles that are arranged annularly around a central axis, as shown in the second and third forms of the invention, the number of nozzles can be increased substantially merely by increasing the diameter of the plates in which the nozzles are mounted so that another annular row can be provided. The nozzles of course can be placed on radial lines, or can be staggered as desired for convenience of construction.

Figure 7:
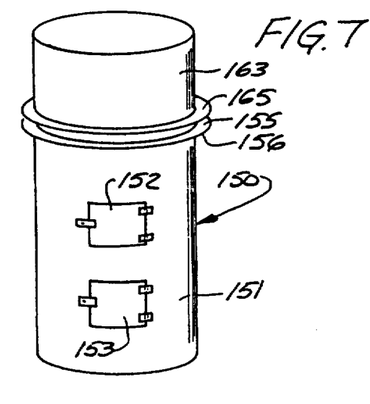
FIG. 7 is a partial perspective view of a modified form of an impactor housing, showing a cylindrical outer housing with access doors for servicing, and also showing the flanged inlet of the present invention.
Figure 8:
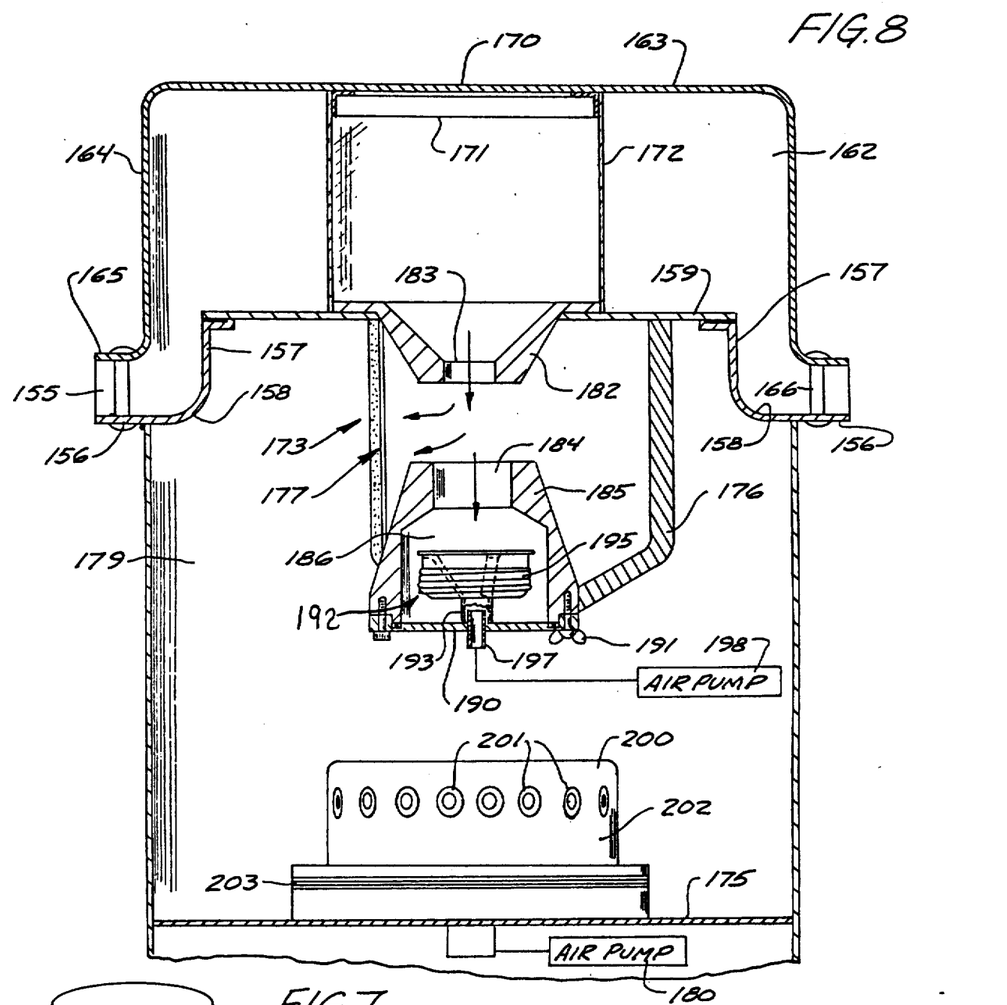
FIG. 8 is a sectional view through the top or upper portions of the device shown in FIG. 7.
Figure 9:
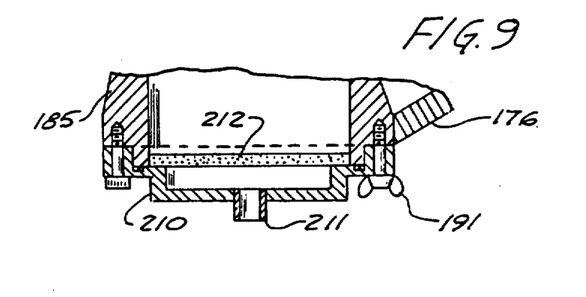
FIG. 9 is a fragmentary sectional view of the lower portion of a primary impactor sampling region showing a different type of filter therein.

Referring now to FIGS. 7, 8 and 9, a high volume impactor housing indicated generally at 150 includes the main support portion 151, that mounts onto a suitable base such as a concrete base on the ground, and as shown is cylindrical in cross section. The support portion 151 extends for the desired height for supporting a standard high volume PM10. As shown, the support portion has first and second access doors 152 and 153 in the walls thereof which permit access to the two different sections of the sampler, as will be shown.

The doors will permit servicing the samplers without disassembling or removing the inlet. The stand or support 151 is used for supporting the particle collecting units that are used for sampling. In this form of the invention, an annular air inlet opening indicated generally at 155 is defined by a lower flange 156 that extends outwardly beyond the periphery of the support 151, and which is an extension of an inner annular wall 157 that has a curved portion 158 and that extends annularly around the inlet. The wall 157 has a top plate 159 attached thereto, and plate 159 forms a divider wall for an upper chamber 162 that is enclosed with a cover 163. The cover 163 has a generally cylindrical outer wall 164, and an outwardly extending annular flange 165 joined to wall 164 which extends parallel to and is spaced from the flange 156. The cover 163 is supported on suitable standoff fastener members 166 that are spaced at intervals, to hold the unit in assembly.

The top wall 170 of the cover has a flange 171 on the interior surface thereof that is used for supporting an annular coarse screen 172 which will prevent leaves and the like from entering into an impactor assembly indicated generally at 173.

As shown in FIG. 8, the interior of the support or stand 151 is divided off with a lower divider wall 175 that defines an upper chamber 179 within the support or stand 151. Chamber 179 is defined between the walls 159 and the wall 175, and the impactor assembly 173 is supported on the wall 159. The support for the receiver tube assembly includes members 176 that extend from the wall 159.

An air pump 180 is provided to draw a major flow of air through an outlet opening in end wall 175, to establish a flow of about 40 cubic feet per minute inwardly through the inlet opening 155, and then upwardly into the chamber 162 defined by the cover 163. The air then flows through a Venturi type downwardly open nozzle 182 that is in the center of the plate 159. Nozzle 182 has a central opening 183 that is centered on the axis of the support or stand 151. Nozzle opening 183 is aligned with an opening 184 in a receiver nozzle 185 that is supported by members 176. The receiver tube 185 has a boundary wall which defines an annular interior chamber 186 of larger diameter than the nozzle that is open toward the bottom, as can be seen. A closure plate 190 is provided across this opening and held in place with suitable screws 191. The closure plate 190 supports a filter assembly 192 on a suitable sleeve 193. The filter is closed tightly around the sleeve 193 so air entering through the opening 184 has to pass through filter 195 to exit the chamber 186.

The closure plate 190 has an outlet conduit 197 therein, and this is connected to a minor flow air pump 198. The conduit 197 opens into the center of sleeve 193. The flow through the pump 198 is preferably in the range of two cubic feet per minute.

The major flow is diverted out through the opening 177 and then passes through filter 203 of an optional second high volume virtual impactor indicated generally at 200, which corresponds structurally to the impactor shown in U.S. Pat. No. 4,670,135. The high volume impactor has a number of inlet nozzles 201 around the periphery of an impactor housing 202. The impactor has a suitable high volume filter assembly 203 through which air will pass to the main air flow pump 180. Particles not separated in the impactor can be collected on the filter 203 in a desired manner, if desired.

The high volume flow of about 40 cubic feet per minute caused by the air pump 180 passes through the filter 203 in the impactor housing 200. There is a very low pressure drop across the impactor 200 because of the high volume capability. The additional impactor assembly provides an additional cutoff size for particles, if desired. For example, the impactor 200 can provide a particle size cutoff of 2.5 microns.

The filter 195 can be changed to a different type by replacing the closure plate 190 with a second closure plate assembly shown in FIG. 9. In FIG. 9, a closure plate 210 has a conduit 211 that corresponds to the conduit 197 and which is connected to the air pump 198. The closure plate 210 is the same size as the plate 190, and has a rim around its periphery. Suitable sealing means can be used, and the plate 210 is held in place with the screws 191. A four-inch round filter indicated at 212 is supported above the plate 210 in this form of the invention. The filter 212 is a standard filter used in particle collection, and may be preferred over that type of filter shown in FIG. 8. When any service is needed for the impactor assemblies, the access doors 152 or 153 can be operated with ease for obtaining access, and the particles that have been collected can then be removed and analyzed easily.

The support 151 is cylindrical, to provide for smooth air flow around the unit. The inlet flow channel is offset to cause a change in direction of flow so that rain being blown into the inlet substantially horizontally will be deflected and permitted to drain out so it will not cause problems with the collection of particles.

The dual stage collection achieved with the previous forms of the invention, such as that shown in FIG. 3, is again achieved with the device of FIGS. 7 and 8.

Because there are no surfaces that are needed for collecting the particles, there is no need for having a porous surface that is coated or impregnated with oil, and omitting an oiled surface minimizes maintenance. The inlet construction is simple, with only an annular inlet opening section and a virtual impactor or classification section needed. Further, the inlet has the advantage of being able to be designed, using known principles, to have exactly the desired 10 micron cut size for the particles.

Although the present invention has been described with reference to preferred embodiments, workers skilled in the art will recognize that changes may be made in form and detail without departing from the spirit and scope of the invention.

What is claim is:

1. An inlet for a high volume sampler for exterior use comprising a filter member through which a standard high volume flow of at least substantially 40 cubic feet per minute passes, including an inlet housing defining a flow path to said filter;

said inlet housing having a generally horizontally facing annular air flow inlet opening defined therein adjacent upper portions thereof; and inertial particle classification means in a series of flow path between the air flow inlet opening and the filter for classifying particles in the high volume flow by size, said inertial particle classification means comprising a virtual impactor with a cutoff for retention of particle below a selected size in the flow path through the filter.

2. The inlet as specified in claim 1 and said nozzle in said housing defining a portion of the flow path and having a conical inlet section leading from said annular inlet opening to accelerate air flowing from the inlet opening and passing through the nozzle.

3. The inlet as specification in claim 2 wherein said air flow inlet opening opens to a passageway defined by an inlet wall that extends upwardly from the inlet opening in a direction to the conical inlet section leading to said nozzle, whereby liquids carried by flow passing through said inlet opening tend to engage said inlet wall and drain back outwardly along said inlet wall.

4. The inlet as specified in claim 1 wherein said filter member is positioned at the bottom of said inlet housing, and a nozzle mounted at an upper end of the inlet housing to accelerate air flow from the inlet opening and provide the air flow through a nozzle outlet, a receiver tube positioned below said nozzle outlet for receiving particles having higher inertial than particle below a size elected by the inertial classification means, and the space between the receiver tube and said nozzle defining a generally horizontally opening space for flow of substantially all of the total flow through the inlet laterally of the receiver tube and for flow of particles carried by the laterally moving air flow.

5. The inlet of claim 2, wherein there is a second virtual impactor between the first mentioned inertial particle classification means and the filter member, the second virtual impactor comprising a plurality of nozzles with each of the nozzles comprising means for a second inertial particle classification, said nozzles being arranged around a central axis in a desired pattern.

6. The inlet as specified in claim 5 wherein said nozzles are mounted adjacent to the inlet opening, said air flow being caused to change direction and flow downwardly through the nozzles before entering the receiver tubes.

7. The inlet of claim 2 wherein a plurality of said nozzles are positioned below a corresponding number of receiver tubes, and the nozzles are above an upper level of the inlet opening, whereby air flows upwardly through said nozzles, and a major portion of the flow passes above the nozzles and receiver tubes, said filter being positioned for filtering the major portion of the flow.

8. The inlet of claim 7 wherein said filter comprises a horizontal filter positioned above the inertial particle separation means, and wherein the air flow passes through a conduit forming a central passage through the inertial particle classification means downwardly to a pump.

9. A high volume particle sampler apparatus comprising:

a frame;

means on the frame providing a first air flow at a desired high flow volume of at least substantially 40 cubic feet per minute;

a filter mounted on said frame so that substantially all of said high volume flow other than a diverted portion, passes through said filter; and an inlet housing leading to said filter including an inlet opening at an end of the housing spaced from said filter, and inertial particle classification means positioned between said inlet opening and said filter, said inertial particle classification means including means for diverting the diverted portion in the range of five percent (5%) of the total flow in a path causing inertial separation of large particles from the flow prior to the time the flow passes through the filter.

10. The apparatus as specified in claim 9 wherein said inlet opening is an annular opening, and the classification means is joined to said annular opening through an annular passageway surrounding said classification means, and whereby said annular passageway inclines upwardly along an upwardly inclined interior wall on the housing defining a surface of the passageway.

11. The apparatus of claim 10 wherein said inlet opening is defined by two overlying flanges, one flange comprising a tope flange, said top flange having a larger diameter than the lower flange to cause rain water which drips off the upper flange to tend to fall clear of the lower flange.

12. The apparatus as specified in claim 9 and course screen means for passage of the flow between the inlet opening and said classifications means.

13. The apparatus of claim 9 wherein the classification means comprises a plurality of nozzle and a plurality of receiver tubes aligned with an spaced from the nozzles, the major portion of the high volume flow passing outwardly through the space between the nozzles and receiver tubes.

14. The apparatus of claim 9 wherein said inertial particle classification means comprises a first nozzle carrying the high volume flow and a second receiver nozzle facing and axially aligned with the first nozzle, and means for establishing a minor flow to carry a part of the high volume flow through the receiver nozzle.

15. The apparatus of claim 14 wherein said nozzle has a housing with a backing plate assembly and filter means carried by the backing plate assembly for filtering the minor flow.

16. The apparatus of claim 15 wherein selectively two different types of filter means are mounted on interchangeable backing plates.

17. The apparatus of claim 9 wherein said inlet housing has a cylindrical exterior, and a divider wall on the interior, said filter being positioned above the divider wall, and a second inertial particle classifications means positioned between the first mentioned inertial classification means and the filter, said second inertial particle classification means having a different cut off size of particles than the first mentioned inertial particle classification means.

18. The apparatus as specified in claim 17 wherein said second inertial particle classification means comprises a housing that has a plurality of inlet nozzles annularly arranged around the housing for providing such inertial classification, and said filter means being mounted below said plurality of nozzles of said second inertial particle classification means.

19. The apparatus of claim 18, wherein said second inertial particle classification means is mounted above said divider wall.

20. The apparatus of claim 17 wherein said inlet housing comprises a cylindrical outer wall and defines an annular inlet opening, said first mentioned inertial particle classification means being positioned adjacent an upper portion thereof, below the annular inlet opening, and the second inertial particle classification means being positioned below the first mentioned inertial classification means, and separate access doors at upper and lower levels from the exterior of the inlet housing for permitting access to the interior of the inlet housing at two different levels.

* * * * *

UNITED STATES PATENT AND TRADEMARK OFFICE
CERTIFICATE OF CORRECTION

PATENT NO.  : 5,040,424
DATED       : August 20, 1991
INVENTOR(S) : Virgil A. Marple et al.

It is certified that error appears in the above-identified patent and that said Letters Patent is hereby corrected as shown below:

Col. 11, line 37, delete "particle", insert --particles--.
Col. 11, line 38, delete "elected", insert --selected--.
Col. 12, line 31, delete "tope", insert --top--
Col. 12, line 39, delete "nozzle", insert --nozzles--.
Col. 12, line 40, delete "an", insert --and--.

Signed and Sealed this

Seventeenth Day of November, 1992

Attest:

DOUGLAS B. COMER

Attesting Officer

Acting Commissioner of Patents and Trademarks